(12) United States Patent
Kan et al.

(10) Patent No.: US 12,064,406 B2
(45) Date of Patent: *Aug. 20, 2024

(54) PHARMACEUTICAL COMPOSITION OF A WEAK ACID DRUG AND METHODS OF ADMINISTRATION

(71) Applicant: Pharmosa Biopharm Inc., Taipei (TW)

(72) Inventors: Pei Kan, Taipei (TW); Yi Fong Lin, New Taipei (TW); Ko Chieh Chen, Taipei (TW)

(73) Assignee: PHARMOSA BIOPHARM INC., Taipei (TW)

( * ) Notice: Subject to any disclaimer, the term of this patent is extended or adjusted under 35 U.S.C. 154(b) by 0 days.

This patent is subject to a terminal disclaimer.

(21) Appl. No.: 15/930,532

(22) Filed: May 13, 2020

(65) Prior Publication Data

US 2020/0360320 A1 Nov. 19, 2020

Related U.S. Application Data

(60) Provisional application No. 62/847,337, filed on May 14, 2019.

(51) Int. Cl.
| | | |
|---|---|---|
| *A61K 31/192* | (2006.01) | |
| *A61K 9/127* | (2006.01) | |
| *A61K 31/191* | (2006.01) | |
| *A61P 9/12* | (2006.01) | |

(52) U.S. Cl.
CPC .......... *A61K 31/192* (2013.01); *A61K 9/127* (2013.01); *A61K 31/191* (2013.01); *A61P 9/12* (2018.01)

(58) Field of Classification Search
CPC .... A61K 31/192; A61K 31/191; A61K 9/127; A61K 9/1271; A61K 9/0078; A61K 47/24; A61K 47/40; A61K 31/557; A61K 31/5578; A61K 47/02; A61P 9/12
See application file for complete search history.

(56) References Cited

U.S. PATENT DOCUMENTS

| | | | |
|---|---|---|---|
| 5,262,168 A | * | 11/1993 | Lenk ...................... A61K 9/127 264/4.3 |
| 5,939,096 A | | 8/1999 | Clerc et al. |
| 8,969,409 B2 | | 3/2015 | Rothblatt et al. |
| | | (Continued) | |

FOREIGN PATENT DOCUMENTS

| | | |
|---|---|---|
| CN | 105164143 A | 12/2015 |
| CN | 105362256 A | 3/2016 |
| | (Continued) | |

OTHER PUBLICATIONS

International Search Report & Written Opinion for PCT/US20/032563, mailed Aug. 11, 2020.

(Continued)

*Primary Examiner* — Gollamudi S Kishore
(74) *Attorney, Agent, or Firm* — Piloff Passino & Cosenza LLP; Rachel K. Piloff; Sean A. Passino

(57) ABSTRACT

The present invention relates to a pharmaceutical composition containing liposomes, said liposome comprise an external lipid bilayer; and an internal aqueous medium including a weak acid drug with a half-life of less than 2 hours. Also provided is the use of the pharmaceutical composition disclosed herein to treat pulmonary hypertension with reduced dosing frequency.

26 Claims, 8 Drawing Sheets

(56) References Cited

U.S. PATENT DOCUMENTS

| | | | |
|---|---|---|---|
| 2006/0029655 A1 | 2/2006 | Barenholz et al. | |
| 2006/0159736 A1* | 7/2006 | Zalipsky | A61K 47/10 |
| | | | 514/23 |
| 2007/0231269 A1* | 10/2007 | Birch | A61P 25/02 |
| | | | 424/43 |
| 2009/0104256 A1 | 4/2009 | Gupta | |
| 2009/0274754 A1 | 11/2009 | Cipolla et al. | |
| 2010/0209538 A1 | 8/2010 | Cipolla et al. | |
| 2011/0064796 A1* | 3/2011 | Cipolla | A61P 31/00 |
| | | | 424/450 |
| 2011/0104052 A1* | 5/2011 | Barnett | A61K 9/1635 |
| | | | 424/1.25 |
| 2011/0224236 A1 | 9/2011 | Rothblatt et al. | |
| 2013/0052259 A1* | 2/2013 | Barenholz | A61P 35/00 |
| | | | 424/450 |
| 2013/0251787 A1* | 9/2013 | Nicolls | A61K 31/197 |
| | | | 424/450 |
| 2013/0273164 A1* | 10/2013 | Minko | A61K 31/5575 |
| | | | 424/489 |
| 2016/0030361 A1 | 2/2016 | Schentag et al. | |
| 2019/0022004 A1 | 1/2019 | Kan | |
| 2019/0160009 A1 | 5/2019 | Huang et al. | |
| 2019/0336461 A1 | 11/2019 | Kan et al. | |

FOREIGN PATENT DOCUMENTS

| | | | |
|---|---|---|---|
| CN | 106214641 A | | 12/2016 |
| CN | 109562068 A | | 4/2019 |
| CN | 112384224 A | | 2/2021 |
| WO | 96/25147 | * | 8/1996 |
| WO | 2014085813 A1 | | 6/2014 |
| WO | 2014152795 A2 | | 9/2014 |
| WO | 2015138423 A1 | | 9/2015 |
| WO | 2016048242 A1 | | 3/2016 |
| WO | 2018/031568 | * | 2/2018 |
| WO | 2018031568 A1 | | 2/2018 |
| WO | 2019023092 A1 | | 1/2019 |

OTHER PUBLICATIONS

Zeenat Safdar, "Treatment of pulmonary arterial hypertension: The role of prostacyclin and prostaglandin analogs," Respiratory Medicine, Jan. 2011, pp. 818-827, vol. 105.
Office Action for related Taiwan application 109115851, mailed Feb. 24, 2021.
Examination Report issued Nov. 29, 2022, in corresponding to Australian Application No. 2020274094, 3 pages.
Office Action issued Dec. 1, 2022, in corresponding to Canadian Application No. 3, 139, 136, 6 pages.
Office Action issued Dec. 14, 2022, in corresponding to European Application No. 20806052.5, 4 pages.
Office Action issued Dec. 6, 2022, in corresponding to Japanese Application No. 2021567850, 8 pages.
Jain et al., "Liposomal nanoparticles encapsulating iloprost exhibit enhanced vasodilation in pulmonary arteries", International Journal of Nanomedicine, vol. 9, No. 1, Jul. 7, 2014, XP055811849, DOI: 10.2147/IJN.S63190, pp. 3249-3261.
Office action dated Oct. 12, 2023, from Rospatent Russian Patent Application No. 2021132189 with translation.
Li, Mingyuan, et al., "Composition design and medical application of liposomes," European Journal of Medicinal Chemistry, Jan. 7, 2019, 164, 641-642 (doi:10.1016/j.ejmech.2019.01.007).
M.D. Mashkovsky, Drugs, 14th edition, vol. 1, Moscow, 2001, p. 11.
Office Action from Saudi Arabia Application No. 521430828, mailed Dec. 13, 2023.
Office Action from China Application No. 202080035303.0, mailed Feb. 23, 2024.
Office Action from Europe Application No. 20 806 052.5, mailed Feb. 27, 2024.
Office Action for Australia Application No. 2020274094, mailed May 8, 2023.
Office Action for Canada Application No. 3,139,136, mailed Jul. 27, 2023.
Office Action for India Application No. 202117051716, mailed Mar. 31, 2022.
Office Action for Indonesia Application No. P00202109889, mailed Apr. 11, 2023.
Office Action for Japan Application No. 2021-567850, mailed May 9, 2023.
Office Action for Japan Application No. 2021-567850, mailed Oct. 24, 2023.
First Office action dated Nov. 8, 2022 from Saudi Arabian application No. SA521430828.
Second Office action dated Jul. 27, 2023 from Saudi Arabian application No. SA521430828.
Office Action for related China application No. 202080035303.0, mailed Sep. 11, 2023.
Yan Ping et al., "Prostacyclin and its analogs in the therapy of pulmonary arterial hypertension," World Clinical Drugs, 2014, pp. 332-337, vol. 35, No. 6.
Search Report and Written Opinion for Singapore Application No. 11202112530V, mailed Nov. 17, 2023.
Hearing Notice for India Application No. 202117051716, mailed Nov. 8, 2023.

* cited by examiner

PHARMACEUTICAL COMPOSITION OF A WEAK ACID DRUG AND METHODS OF ADMINISTRATION

CROSS-REFERENCE TO RELATED APPLICATIONS

This application claims the benefit of U.S. Application No. 62/847,337 filed on 14 May 2019, the entire disclosure of which is incorporated herein by reference.

FIELD

Disclosed herein are pharmaceutical compositions, comprising at least one liposome encapsulating a weak acid drug with a half-life less than 2 hours, formulated to yield a peak to trough drug plasma concentration ratio (P/T ratio) of 1 to 100 (i.e., a flatter plasma profile) and/or increase the potency of the encapsulated weak acid drug compared to that of a free weak acid drug.

BACKGROUND

Pulmonary hypertension (PH), defined as a mean pulmonary arterial pressure (PAP) greater than 25 mm Hg at rest or greater than 30 mm Hg during exercise, is often characterized by a progressive and sustained increase in pulmonary vascular resistance. It may eventually lead to right ventricular failure and can be a life-threatening condition if untreated. The World Health Organization (WHO) has divided PH into five groups on the basis pathophysiology, clinical presentation, and therapeutic options. [J Am Coll Cardiol. 2009; 54(1 Suppl):S43-54].

PH (WHO Group 1) is a condition characterized by an increase in blood pressure in the pulmonary artery, pulmonary vein, or pulmonary capillaries, leading to shortness of breath, dizziness, fainting, and other symptoms, all of which are exacerbated by exertion. PH is a severe disease with a markedly decreased exercise tolerance and heart failure. It is an orphan disease with an incidence of 500-1000 new cases in the US. Median survival of patients with untreated PH is in the range of 2-3 years from the time of diagnosis, with the cause of death usually being right ventricular failure.

Administering a therapeutic agent to treat PH by inhalation has many advantages, including the direct delivery of the therapeutic agent to the target organ, thus enhancing pulmonary specificity and reducing systemic adverse effects. It can also improve ventilation/perfusion matching due to vasodilatation and improved gas exchange and lead to a higher drug concentration at the target organ with a lower overall dose. A number of therapeutic agents for treating PH, such as prostaglandin and its derivatives, have been approved by the FDA. The drawbacks of inhaled prostaglandins are wide fluctuation in drug plasma level between the doses and the short half-lives of prostaglandin. These drawbacks require frequent drug inhalation (once every 4 hours, 4-6 times a day) and increase systemic side effects (e.g. headache, nausea, flushing, and dizziness) and local irritations (such as cough, throat irritation, pharyngeal pain, epistaxis, hemoptysis and wheezing), which ultimate lead to intolerance of inhaled prostaglandins (N S Hill et al, Inhaled Therapies for Pulmonary Hypertension. Respir Care 2015 June; 60(6):794-802).

Therefore, there is a need for an inhalation therapy for PH which provides a prolonged therapeutic effect and/or enhanced potency yet reduces the administration frequency. The present invention addresses these needs and other needs.

BRIEF SUMMARY OF THE INVENTION

The present invention provides a pharmaceutical composition comprising liposomes suspended in an external medium, said liposomes comprising (a) an external lipid bilayer, comprising at least one vesicle-forming phospholipid; and (b) an internal aqueous medium, comprising a weak acid drug with a half-life less than 2 hours and a salt to provide a pH gradient between the internal aqueous medium and the external medium, and following administration of the pharmaceutical composition at least every six hours produces a peak to trough drug plasma concentration ratio (P/T ratio) of about 1 to about 100.

The present invention also discloses methods of treating pulmonary hypertension, comprising the steps of administering the pharmaceutical composition described herein at least every 6 hours.

The invention will become more apparent when read with the accompanying figures and detailed description which follow.

BRIEF DESCRIPTION OF THE DRAWINGS

Illustrative embodiments of the present invention are described in detail below with reference to the following figures.

DETAIL DESCRIPTION OF INVENTION

Figure 1A:
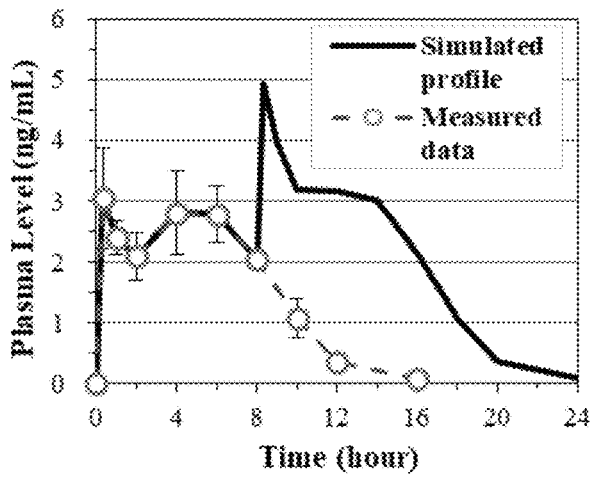
FIG. 1A-FIG. 1D are line graphs illustrating the simulated and measured treprostinil plasma levels of the liposomal treprostinil composition in rats at different dosing frequencies (FIG. 1A is 8 hours BID, FIG. 1B is 10 hours BID, FIG. 1C is 12 hours BID and FIG. 1D is 8 hours TID).
Figure 1B:
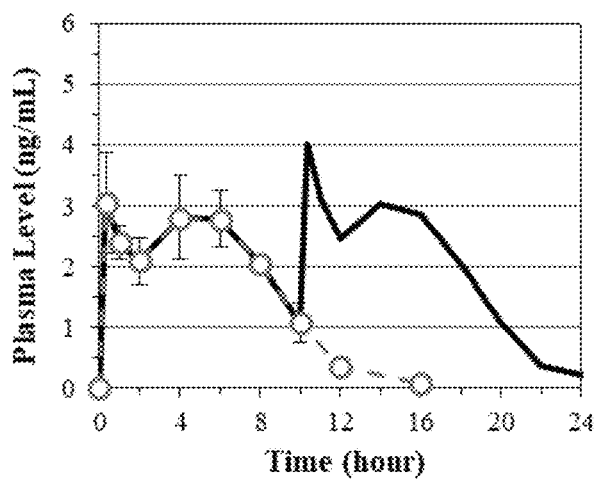
Figure 1C:
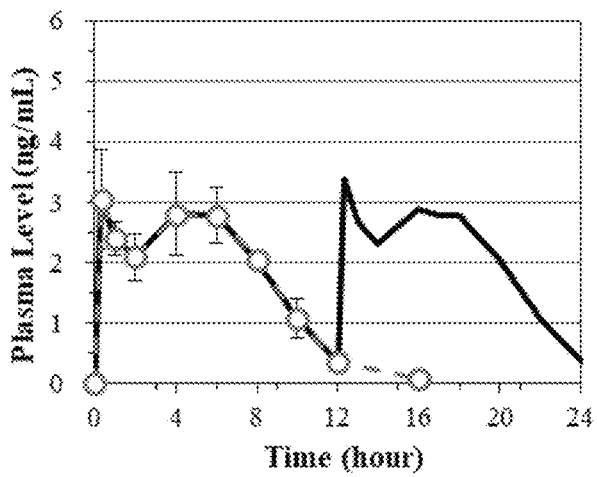
Figure 1D:
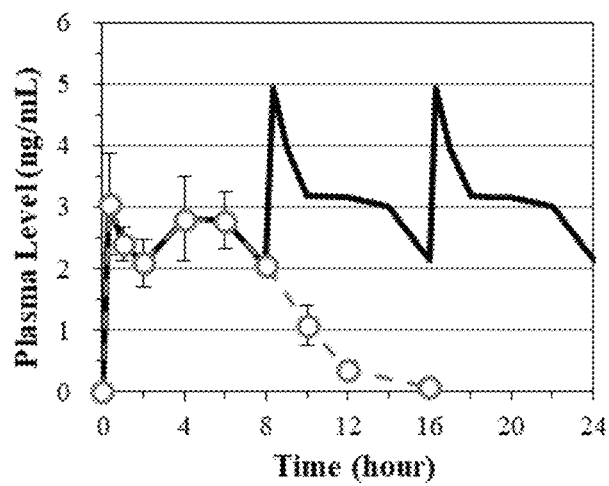
Figure 1E:
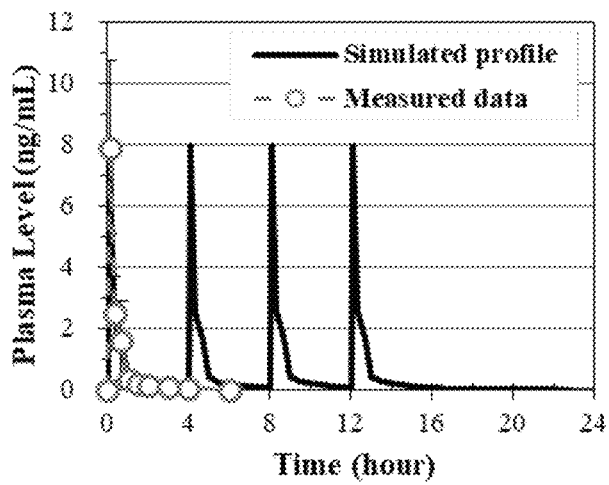
FIG. 1E is the line graph illustrating the simulated and measured treprostinil plasma levels of the free treprostinil solution in rats administered every 4 hours, QID.

As used herein, the articles "a" and "an" refer to one or more than one (i.e., at least one) of the grammatical object of the article. By way of example, "an element" means one element or more than one element.

All numbers are modified by the term "about". As used herein, the term "about" refers to a range of ±10% of a specified value.

The term "comprise" or "comprising" is generally used in the sense of include/including which means permitting the presence of one or more features, ingredients or components.

The term "subject" can refer to a vertebrate having pulmonary hypertension or to a vertebrate deemed to be in need of treatment for pulmonary hypertension. Subjects include warm-blooded animals, such as mammals, such as a primate, and, more preferably, a human. Non-human primates are subjects as well. The term subject includes domesticated animals, such as cats, dogs, etc., livestock (for example, cattle, horses, pigs, sheep, goats, etc.) and laboratory animals (for example, mouse, rabbit, rat, gerbil, guinea pig, etc.). Thus, veterinary uses and medical formulations are contemplated herein.

The term "treating" refers to both therapeutic treatment and prophylactic or preventative measures. Those in need of treatment include those already with PH, those prone to having PH due to conditions such as chronic pulmonary emboli, pulmonary fibrosis, chronic obstructive pulmonary disease (COPD) or those in which PH is to be prevented. The application or administration of the pharmaceutical composition described herein aims to cure, heal, alleviate, relieve, alter, remedy, ameliorate, improve, or affect PH, the symptoms or conditions of PH, the disabilities induced by PH, or the progression of PH.

As used herein, the terms "encapsulation", "loaded" and "entrapped" can be used interchangeably, and refer to the incorporation or association of a biologically active agent (e.g., iloprost) in the internal aqueous medium of a liposome.

As used herein, "substantially free" means that pharmaceutical composition contains less than 5%, 4%, 3%, 2% or 1% of a specific substance. In some embodiments, pharmaceutical composition does not contain the specific substance.

The term "drug potency" is defined as AUC (area under the curve) of PAP reduction÷AUC of the drug plasma concentration.

A weak acid drug as used herein, unless indicated to the contrary or otherwise evident from the context, also include its pharmaceutically acceptable salt and its protonated form. In one embodiment, the weak acid drug has a half-life of 1 minute to 2 hours, 1 minute to 1.5 hours, 1 minute to 1 hour, 10 minutes to 2 hours or 30 minutes to 2 hours. In another embodiment, a weak acid drug has a pKa between 1 to 7, between 1 to 6, between 2 to 6, between 2 to 6.9, between 2.5 to 7 or between 2.5 to 6. In yet another embodiment, the weak acid drug is prostaglandin. Table 1 shows the non-limiting examples of the weak acid drug with a half-life less than 2 hours.

TABLE 1

Weak acid drugs suitable in the present invention

| Drug category | Drug species |
| --- | --- |
| Prostaglandin or its analogues | Prostaglandin E1 (PGE1)<br>Prostaglandin E2 (PGE2) e.g., dinoprostone<br>Epoprostenol<br>Iloprost (prostacyclin analog)<br>Beraprost (prostacyclin analog)<br>Treprostinil (prostacyclin analog) |

In one embodiment, the weak acid drug with a half-life less than 2 hours is not a prodrug. In another embodiment, the weak acid drug is substantially free of a carrier, such as a polymer, a hydrogel or a well hydrated polymer matrix. Without being bind by any particular theory, it is believed the combination of a carrier and a weak acid with a half-life less than 2 hours (e.g., polymer and treprostinil) is not suitable for inhalation as the drug may not be released from the polymer and accumulates in the lung, leading to unwanted side effects. Nor is such combination suitable for parenteral administration as it causes clotting.

The present invention provides a controlled released pharmaceutical composition with a flatter plasma profile, comprising liposomes suspended in an external medium, said liposomes comprising: (a) an external lipid bilayer, comprising at least one vesicle-forming phospholipid; and (b) an internal aqueous medium, comprising a weak acid drug with a half-life less than 2 hours and a weak acid salt to provide a pH gradient between the internal aqueous medium and the external medium, wherein following administration of the pharmaceutical composition at least every six hours, produces a P/T ratio of about 1 to about 100.

As used herein, the term "P/T ratio" is intended to mean the ratio between a peak plasma level (e.g., highest steady state plasma concentration) of a weak acid drug between at least two doses and a trough plasma level (e.g., lowest steady state plasma concentration) of a weak acid drug between at least two doses. A narrower P/T ratio, for example, less than 100, 90, 80, 70, 60, 50, 40, and a flatter plasma profile sustain the therapeutic effects for at least 6 hours and lessen the dosing frequency of the weak acid drug.

The P/T ratio of the pharmaceutical composition is less than 100, about 10-100, 10-95, 10-90, 10-85, 10-80, 10-75, 10-70, 10-65, 10-60, 10-55, 10-50, 5-100, 5-95, 5-90, 5-85, 5-80, 5-75, 5-70, 5-65, 5-60, 5-55, 5-50, 2-100, 2-95, 2-90, 2-85, 2-80, 2-75, 2-70, 2-65, 2-60, 2-55, 2-50, 1-100, 1-95, 1-90, 1-85, 1-80, 1-75, 1-70, 1-65, 1-60, 1-55, 1-50, 1-45, 1-40, 1-39, 1-38, 1-37, 1-36, 1-35, 1-34, 1-33, 1-32, 1-31, 1-30, 1-29, 1-28, 1-27, 1-26, 1-25, 1-24, 1-23, 1-22, 1-21, 1-20, or any range therein between (e.g., 5-40) with a dosing frequency at least every 6 hours whereas the P/T ratio of the corresponding free drug (e.g., treprostinil and iloprost) is over 100 with a dosing frequency less than every 6 hours.

In an exemplary embodiment, the P/T ratio of iloprost encapsulated in the pharmaceutical composition is about 5 to about 40 with dosing regimen of every 6, 8, 10 or 12 hours. In another exemplary embodiment, the P/T ratio of treprostinil encapsulated in the pharmaceutical composition is about 1 to about 20 with dosing regimen of every 6, 8, 10 or 12 hours.

The pharmaceutical composition of the present invention with the claimed P/T ratio has the following characteristics:
Increases PAP reduction and enhances the potency of the weak acid drug. The potency of the pharmaceutical composition is 2, 3, 4, 5, 6, 7, 8, 9, 10, 11, 12, 13, 14 or 15 times higher than that of the free weak acid drug. Without being bound by any particular theory, it is believed the initial spiked plasma level and/or the high P/T ratio of a weak acid drug (e.g., prostacyclin and/or its analogs) mediate both vasoconstriction and vasodilatation, through activation of different prostanoid receptor subtypes. Accordingly, a weak acid drug with a high P/T ratio leads to a higher peak drug concentration in the plasma, and hence, less PAP reduction due to the activation of vasoconstriction receptors (e.g. $DP_1$, IP, $EP_2$ and $EP_4$) which constrict the pulmonary vasculature. On the other hand, a weak acid drug with a lower P/T ratio (e.g., less than 100) avoids the initial spike in drug plasma concentration (i.e., a flatter plasma profile), and hence, more PAP reduction and increased drug potency due to the activation of vasodilatation receptors (e.g. $EP_3$, $EP_1$ and FP) only, which dilate the pulmonary vasculature.

The therapeutically effect of the weak acid drug is maintained for at least 6 hours after a single administration of the pharmaceutical composition and hence, reduces the administration frequency (i.e., 1-3 times daily) and reduces the side effects.

In an exemplary embodiment, the therapeutic effect of treprostinil is maintained for 6-12 hours. In another exemplary embodiment, the therapeutic effect of iloprost is maintained for at least 6 hours.

A higher drug concentration (e.g., higher than 1.0 mg/mL of prostacyclin or its analogs) in the pharmaceutical composition allows a higher amount of drug be delivered in a given time (e.g., 0.45 mg treprostinil can be delivered per min) compared to that of the free drug compared to that of the free drug (0.18 mg treprostinil per min), without inducing the initial spike of drug plasma concentration.

The present invention further provides methods for treating PH, by administering a therapeutic effective amount of the pharmaceutical composition described herein.

The "therapeutically effective amount" used herein refers to the amount of the weak acid drug to confer a therapeutic effect in a subject with PH and may change depending on various factors, such as administration route and frequency, body weight and age. Persons skilled in the art may determine the dosage in each case based on the disclosure herein, established methods, and their own experience. The term "therapeutic effect" refers to at least 20% PAP reduction from the base line.

The pharmaceutical composition described herein may be administered orally, by inhalation, injection (for example, intraarterialy, intravenously, intraperitoneally, subcutaneously, intra-vitreally, intrathecally, intraarticularly, intramuscularly, within other human body cavities). In some embodiments, inhalation is administered via a metered dose inhaler, a dry powder inhaler, a nebulizer, a soft mist inhaler or dispersing via aerosol (including intranasal and pulmonary administration).

In some embodiments, the pharmaceutical composition may be administrated once to three times a day. In other embodiment, the frequency of dosing of the pharmaceutical composition can be about every 6 hours, 6.5 hours, 7, hours, 7.5 hours, 8 hours, 8.5 hours, 9 hours, 9.5 hours, 10 hours 10.5 hours, 11 hours, 11.5 hours, 12 hours or some mixture thereof.

In some embodiments, the pharmaceutical composition is administered with another therapeutic agent for treating PH. Non limiting examples of the therapeutic agent for treating PH include PDE-5 inhibitor, calcium channel blocker, endothelin receptor antagonist, guanylate cyclase stimulators, anti-coagulant, or a combination thereof Liposomal Components The term "liposome" as used herein refers to microscopic vesicles or particles made up of one or more lipid bilayers enclosing an internal aqueous medium. To form liposomes, the presence of at least one "vesicle-forming lipid" is needed, which is an amphipathic lipid capable of either forming or being incorporated into a lipid bilayer. Any suitable vesicle-forming lipid may be used to form the lipid bilayer constituting the liposomes. Vesicle-forming lipid includes, but not limited to, phospholipids such as phosphatidylcholine (PC), phosphatidylglycerol (PG), phosphatidylinositol (PI), phosphatidic acid (PA), phosphatidylethanolamine (PE) or phosphatidylserine (PS), and charged lipids, such as a positively charge lipid or a negatively charged lipid.

The lipid bilayer of the liposome further comprises sterol (e.g., 0-14.99 mole %), said sterol is selected from the group consisting of cholesterol, cholesterol hexasuccinate, ergosterol, lanosterol, and any combination thereof, but is not limited thereto. In an exemplary embodiment, the sterol is cholesterol.

In some embodiments, the vesicle-forming lipid is a mixture of a first phospholipid and a second phospholipid. In certain embodiments, the first phospholipid is phosphatidylcholine (PC), which is selected from the group consisting of hydrogenated egg phosphatidylcholine (HEPC), hydrogenated soy phosphatidylcholine (HSPC), dipalmitoyl phosphatidylcholine (DPPC), distearyloyl phosphatidylcholine (DSPC), diarachidoyl phosphatidylcholine, dimyristoyl phosphatidylcholine (DMPC), egg phosphatidylcholine (EPC), soy phosphatidylcholine (SPC), oleoyl palmitoyl phosphatidylcholine, dioleoyl phosphatidylcholine (DOPC), dipetroselinoyl phosphatidylcholine, palmitoylelaidoyl phosphatidylcholine, palmitoyloleoyl phosphatidylcholine, dilauroyl phosphatidylcholine (DLPC), diundecanoyl phosphatidylcholine, didecanoyl phosphatidylcholine, dinonanoyl phosphatidylcholine, and any combination thereof. In other embodiments, the second phospholipid is a polyethylene glycol modified phospholipid, containing a polyethylene glycol having a molecular weight of about 500 to about 10,000 daltons, such as 1,2-distearoly-sn-glycero-3-phosphoethanolamine-N-[methoxy(polyethylene glycol)-2000] (DSPE-PEG2000), a negatively charged phospholipid, such as distearyloyl phosphatidylglycerol (DSPG), Dipalmitoylphosphatidylglycerol (DPPG) or dimyristoylphosphatidylglycerol (DMPG) or dioleoyl phosphatidylglycerol (DOPG). In an exemplary embodiment, the mole percent of the first phospholipid:cholesterol:the second phospholipid is 75-99:0-14.9:0.1-25.

In other embodiments, the vesicle-forming lipids are a mixture of a first phospholipid and a charged lipid. In an exemplary embodiment, vesicle-forming lipids are a mixture of a first phospholipid, a second phospholipid and a charged lipid. The charged lipid, includes stearylamine, 1,2-dioleoyl-3-trimethylammonium-propane (DOTAP), 3ß-[N—(N',N'-dimethylaminoethane)-carbamoyl]cholesterol (DC-Cholesterol), $N^4$—Cholesteryl-Spermine (GL67), dimethyldioctadecylammonium (DDAB), 1,2-di-O-octadecenyl-3-trimethylammonium propane (DOTMA), ethylphosphocholine (ethyl PC) or combination thereof. In another exemplary embodiment, the mole percent of the first phospholipid:cholesterol:charged lipid is 75-99:0-14.9:0.1-25.

In an embodiment, the mole % of HSPC, cholesterol, and DSPG in the lipid bilayer is 75-99:0-14.9:0.1-25. In another embodiment, the mole % of HSPC, cholesterol and DSPE-PEG2000 in the lipid bilayer is 75-99:0-14.9:0.1-25.

In one embodiment, the external lipid bilayer of the liposomes further comprises a surfactant, which can be a non-ionic surfactant, a cationic surfactant or a zwitterionic surfactant. A non-ionic surfactant has no formally charged groups in its head. A cationic surfactant carries a net positive charge in its head. A zwitterion surfactant is electrically neutral but carries formal positive and negative charges on different atoms.

Non-limiting examples of non-ionic surfactant include non-ionic water soluble mono-, di-, and tri-glycerides; non-ionic water soluble mono- and di-fatty acid esters of poly-ethyelene glycol; non-ionic water soluble sorbitan fatty acid esters (e.g. sorbitan monooleates such as TWEEN 20 (poly-oxyethylene 20 sorbitan monooleate), SPAN 80); non-ionic water soluble triblock copolymers (e.g., poly(ethyleneoxide)/poly-(propyleneoxide)/poly(ethyleneoxide) triblock copolymers such as POLOXAMER 406 (PLURONIC F-127), or derivatives thereof.

Non-limiting examples of cationic surfactant include dimethyldialkylammonium bromide or dodecyltrimethylammonium bromide.

Non-limiting examples of zwitterionic surfactant include 3-(N,N-dimethyl palmitylammonio)-propanesulfonate.

The liposome in the suspension is subjected to size reduction. A liposome's size is typically referred to its diameter. Liposome size reduction can be accomplished by a number of methods, such as extrusion, sonication, homogenization techniques or milling techniques, which are well known and can be performed by persons skilled in this art. Extrusion includes passing liposomes, under pressure, one or more times through filters having defined pore sizes. The filters are generally made of polycarbonate, but can also be made of any durable material which does not interact with the liposomes and which is sufficiently strong to allow extrusion under sufficient pressure. The size of the liposomes can be reduced by sonication, which employs sonic energy to disrupt or shear liposomes that will spontaneously reform into smaller liposomes. For example, sonication can be conducted by immersing a glass tube containing the liposome suspension into the sonic epicenter produced in a bath-type sonicator, or a probe type sonicator may be used in which the sonic energy is generated by vibration of a titanium probe in direct contact with the liposome suspension. In the present invention, the liposomes generally have a diameter of about 50 nm to 500 nm, such as about 500 nm or less, about 400 nm or less, about 300 nm or less, about 200 nm or less or about 100 nm or less.

After sizing, the concentration of the weak acid salt in the external medium is adjusted to provide a pH gradient between the internal aqueous medium and the external medium, which can be carried out by a number of ways, for example, by exchanging the external medium with a suitable buffer lacking the weak acid salts such as citric acid buffer ($H_3C_6H_5O$) and phosphoric acid buffer ($H_3PO_4$), by methods such as diafiltration, dialysis, ultrafiltration, or tangential flow filtration.

The weak acid salt provides a lower outside and a higher inside pH gradient between the external medium and the internal aqueous medium of the liposomes. In one embodiment, the pH of the external medium pH is at least 0.1 unit, 0.5 unit or 1 unit higher than the pKa of the weak acid drug. In yet another embodiment, the pH of the internal aqueous medium is about 7, 8, 9 or 10 and the pH of the external medium is less than 7, less than 6, less than 5, less than 4, less than 3, about 3-7, about 3.5-6.5, or about 4-6.

Non-limiting examples of weak acid salt include carboxylic acid salt and bicarbonate salt.

"Bicarbonate salt" as used herein refers to a pharmaceutically acceptable salt compound including a bicarbonate anion and a cationic component. In one embodiment, the cationic component of the salt compound is a metal. Non-limiting examples of the metal include a Group IA or IIA metal, such as potassium (K), sodium (Na), calcium (Ca), magnesium (Mg), cesium (Cs), and lithium (Li) or a metal other than Group IA or IIA metal, such as ferrous iron (Fe) and nickel (Ni). Examples of bicarbonate salt include, but not limited to, potassium bicarbonate, sodium bicarbonate, calcium bicarbonate, magnesium bicarbonate, cesium bicarbonate, lithium bicarbonate, nickel bicarbonate, ferrous iron bicarbonate or any combination thereof.

"Carboxylic acid salt" as used herein includes, but not limited to, formate, acetate, propionate, butyrate, isobutyrate, valerate, isovalerate or a combination thereof. In one exemplary embodiment, the acetate is sodium acetate, calcium acetate, or a combination thereof The concentration of the bicarbonate salt or carboxylic acid salt is 50 mM or above, 100 mM or above, 150 mM or above, 200 mM or above, 250 mM or above, 300 mM or above, 350 mM or above, 400 mM or above, 450 mM or above, 500 mM or above, 600 mM or above, 700 M or above, 800 mM or above 900 mM, less than 1000 mM, from 50 mM to less than 1000 mM, from 50 mM to 800 mM, from 200 mM to less than 1000 mM, from 200 mM to 800 mM, or from 200 mM to 600 mM, from 250 mM to less than 1000 mM, from 250 mM to 800 mM, or from 250 mM to 600 mM, from 300 mM to 600 mM.

The prepared liposome can be stored for substantial periods of time prior to weak acid drug loading and administration to a subject. For example, liposomes can be stored at refrigerated conditions for substantial periods of time prior to weak acid drug loading. Alternatively, liposomes can be dehydrated, stored, and subsequently rehydrated and loaded with a weak acid drug prior to administration. Liposomes may also be dehydrated after being loaded with the weak acid drug. Dehydration can be performed by a number of methods available and known in the art. In some embodiments, liposomes are dehydrated using standard freeze-drying apparatus i.e. dehydration under low pressure conditions. Also, liposomes can be frozen e.g. using liquid nitrogen. Saccharides can be added to the liposomal environment, e.g., to the buffer containing the liposomes, prior to dehydration, to ensure stability and integrity of the liposome during dehydration. Examples of saccharides include but are not limited to maltose, lactose, sucrose, trehalose, dextrose, sorbitol, mannitol, xylitol, or a combination thereof.

The present disclosure will be further described in the following examples. However, it should be understood that the following examples are solely intended for the purpose of illustration and should not be construed as limiting the present disclosure in practice.

EXAMPLES

Liposomal Treprostinil Composition

A liposomal colloidal suspension was prepared using ethanol injection technique as follows.

All lipid ingredients including a first phospholipid (i.e., HSPC), cholesterol and a second phospholipid (i.e., DSPG) at a molar ratio of 3:2:0.075 were dissolved in 2.86 mL of ethanol solution at approximately 60° C. The resultant lipid solution was then injected into 17.14 mL sodium bicarbonate solution (400 mM; pH 8.5) and mixed under vigorous stirring at 60° C. for liposome hydration, followed by extrusion 6 to 10 times through polycarbonate membranes with specific pore size (200 and/or 100 nm, respectively). A suspension of liposomes having a mean particle size of 100 nm to 140 nm and a polydispersity index (PdI) of <0.2 was obtained. The suspension of liposomes was dialyzed with a tangential flow filtration system against 50 mM of sodium citrate buffer (pH 5.5) to form a transmembrane pH gradient between the internal aqueous core of the liposome and the external medium (i.e., a higher inside and lower outside pH gradient) and then stored at 4° C. before drug loading.

Treprostinil (commercially available from Cayman Chemical, USA) was dissolved in 50 mM of sodium citrate aqueous solution, then added into the suspension of liposomes of the preceding paragraph at a drug-to-phospholipid ratio of 1.5 mg/mL-to-10 mM and incubated at 40° C. for 30 min. The resultant product was adjusted with a sodium citrate buffer (pH 5.5) to obtain a liposomal treprostinil composition with a pH of 5.5 in the external medium and a phospholipid concentration of 8.59 mg/mL.

Liposomal Iloprost Composition

A liposomal colloidal suspension was prepared using ethanol injection technique as follows.

All lipid ingredients including a first phospholipid (i.e., HSPC) and a second phospholipid (i.e., DSPE-PEG2000) at a molar ratio of 98:2 were dissolved in 2.86 mL of ethanol solution at approximately 60° C. The resultant lipid solution was then injected into 17.14 mL sodium bicarbonate solution (200 mM; pH 8.5) that contains cyclodextrin (i.e., hydroxypropyl-β-cyclodextrin (90 mM)) and mixed under vigorous stirring at 60° C. for liposome hydration, followed by extrusion through polycarbonate membranes with specific pore size (200 and/or 100 nm, respectively) 6 to 10 times. A suspension of liposomes having a mean particle size of 100 nm to 140 nm and a polydispersity index (PdI) of <0.02 was obtained. The suspension of liposomes was dialyzed with a tangential flow filtration system against 10 mM of sodium citrate buffer (pH 5.5) to form a transmembrane pH gradient between the internal aqueous core of the liposome and the external medium (i.e., a higher inside and lower outside pH gradient) and then stored at 4° C. before drug loading.

Iloprost (commercially available from Cayman Chemical, USA) was dissolved in 50 mM of sodium citrate aqueous solution, then added into the suspension of liposomes of the preceding paragraph at a drug-to-phospholipid ratio of 0.25 mg/mL-to-10 mM and incubated at 40° C. for 30 min. The resultant product was adjusted with sodium citrate buffer (pH 5.5) to obtain a liposomal iloprost composition with a pH of 5.5 in the external medium and a phospholipid concentration of 8.59 mg/mL.

Preparation of Free Treprostinil Solution

Free treprostinil solution was prepared by dissolving 0.6 mg treprostinil in 10 mL solution that contains 6.52 mg/mL of sodium chloride, 6.31 mg/mL of sodium citrate and 0.2 mg/mL of sodium hydroxide. The pH of the solution was adjusted to 6.0-7.2 using 1N hydrochloric acid.

Preparation of Free Iloprost Solution

Free iloprost solution was prepared by dissolving 0.02 mg iloprost in 10 mL of solution that contains 1.62 mg/mL of ethanol, 0.242 mg/mL of tromethamine and 9.0 mg/mL of sodium chloride.

Analytical Method of Treprostinil Concentration

The analysis of treprostinil concentration in the liposomal treprostinil composition or the free treprostinil solution was performed using Waters HPLC system with PDA Detector. An aliquot of 20 μL of the sample solution was directly injected into the HPLC system with a mixture of acetonitrile and phosphate buffer (pH 2.5) at volume ratio of 50:50 as the mobile phase at flow rate of 1.0 mL/min. Separation was performed in $C_{18}$ column, 4.6 mm×7.5 cm, 3.5 at 45° C. and the peak was detected at 220 nm.

Analytical Method of Iloprost Concentration

The analysis of iloprost concentration in the liposomal iloprost composition or the free iloprost solution was performed using Waters HPLC system with PDA Detector. An aliquot of 30 μL of the sample solution was directly injected into the HPLC system with a mixture of acetonitrile, methanol, phosphate buffer (pH 2.5) at volume ratio of 36:17:47 as the mobile phase at flow rate of 1.0 mL/min. Separation was performed in 3.9 mm×15.0 cm, 5.0 at 25° C. and the peak was detected at 205 nm.

Measured Pharmacokinetic (PK) Profile in Rats

Test article (liposomal compositions comprising treprostinil or iloprost, free treprostinil solution or iloprost solution) was administered to the study animal by a microspray aerosol device (MicroSprayer, PennCentury, Philadelphia, PA) attached to a high-pressure syringe (PennCentury). Each Sprague Dawley rat (>250 g) was anesthetized with isofluran and positioned securely at a 45° to 50° angle by the upper teeth. The microspray aerosol tip was inserted to the trachea bifurcation and 0.5 mL/kg of the test article was administered.

At each predetermined time point, a blood sample of the rat was collected into a heparin-containing tube and maintained on wet ice. The blood sample was then centrifuged at approximately 2500×g for 15 min and at 4±2° C. within 1 hour of collection, so as to separate the plasma from the blood cells. Approximately 0.1 mL of the plasma sample was added into a new storage tube and stored at −70±2° C.

Plasma treprostinil concentration was measured by mixing 50 μL of the plasma sample with 150 μL of acetonitrile and vortexed the mixture for 1 minute to disrupt the binding of plasma proteins to treprostinil, followed by centrifugation at 3000 rpm for 5 minutes. The supernatant (150 μL) was mixed with an equal volume of $H_2O$ and subjected to a liquid chromatography-tandem mass spectrometry (LC-MS/MS) analysis (Table 2).

Plasma iloprost concentration was determined by mixing 30 μL of the plasma sample with 3 mL methyl tert-butyl ether and vortex-mixed for 1 minute. 1 mL of formic acid solution (2%) was then added and the resultant mixture was vortexed for 2 minute to disrupt the binding of plasma proteins to iloprost, followed by centrifugation at 3000 rpm for 5 minutes. The supernatant (150 μL) was transferred to a clean tube, evaporated to dry under $N_2$ Stream for 15 min at 35° C., mixed with 200 μL of $H_2O$ and subjected to a LC-MS/MS analysis (Table 2).

TABLE 2

| Rat plasma analytical method information | | |
|---|---|---|
| Item | Description | |
| Analyte | Treprostinil | Iloprost |
| Analytical technique | LC-MS/MS | LC-MS/MS |
| Species | Rat | Rat |
| Analytical matrix | Plasma | Plasma |
| Internal standard (ISTD) | Losartan (0.01 ng/μL in ACN) | Topiramate (0.02 ng/μL in MeOH) |

TABLE 2-continued

Rat plasma analytical method information

| Item | Description | |
|---|---|---|
| Quantification range | 0.025-10 ng/mL | 0.1-10 ng/mL |
| Quality Control (QC) levels | 0.075 ng/mL, 5 ng/mL, 8 ng/mL | 0.030 ng/mL, 5 ng/mL, 8 ng/mL |
| Sample volume | 10.0 μL | 10.0 μL |
| Calibration model | Linear regression | Linear regression |
| Weighting factor | $1/x^2$ | $1/x^2$ |

Measured Pharmacokinetic (PK) Profile in Healthy Human

Liposomal treprostinil composition was administered to healthy human subjects (emitted does 51 μg; n=6) using Micro nebulizers (Philips Health Care, Chichester, UK). Treprostinil plasma concentrations were assessed at predetermined time points after inhalation. Treprostinil was isolated through liquid/liquid extraction, the supernatant was evaporated under a nitrogen stream and the remaining residue was reconstituted. The final extract was analyzed via UPLC and MS/MS detection (Table 3).

TABLE 3

Treprostinil plasma analytical method in human

| Item | Description |
|---|---|
| Analyte | Treprostinil |
| Analytical technique | UPLC-MS/MS |
| Species | Human |
| Analytical matrix | Plasma |
| Internal standard (ISTD) | Treprostinil-$d_9$ |
| Quantification range | 0.0250-10 ng/mL |
| Quality Control (QC) levels | 0.060, 0.150, 0.500, ng/mL 1.50 and 7.50 |
| Sample volume | 100.0 μL |
| Calibration model | Linear regression |
| Weighting factor | $1/x^2$ |

Pharmacokinetics (PK) and Pharmacodynamics (PD) Assessment in Conscious Acute PH Rat Model Induction of Acute PH in Rats Male Sprague Dawley rats weighing approximately 300-350 g were used for this study. One end of a pressure catheter was inserted into the pulmonary artery (PA) of the rat to measure the pressure. The other end of the catheter was exposed at the nape of the neck and connected to a pressure transducer. On the following day, rats were transferred to a hypoxic chamber (oxygen level was 10%/$FiO_2$=0.1). To induce persistent PH, rats were left in the hypoxic chamber overnight. Once PH was established, a microsprayer was used to deliver the test article just above the trachea bifurcation. PAP was measured continuously for 30 seconds (to calculate the mean PAP) and blood sample was collected at each predetermined time point.

Simulated Plasma Profile

The simulated plasma profile was computed using the linear internal method based on the measured drug plasma level in rats or human after a specific period (i.e., 8, 10 and 12 hours after inhalation).

Example 1: The Effect of Liposomal Treprostinil Composition on Treprostinil Plasma Level in Healthy Rats FIGS. 1A to 1D show the measured and simulated PK profiles of liposomal treprostinil compositions in rats at different dosing frequencies. Treprostinil plasma level was between 2.0 to 3.0 ng/mL for up to 8 hours and decreased to 0.3 ng/mL 12 hours after intra-tracheal administration of 48 μg/kg of liposomal treprostinil composition (see Measured Data in FIG. 1A to 1D). Therefore, the liposomal treprostinil composition of the present invention can be delivered twice a day (BID, every 8, 10 or 12 hours) or three times a day (TID, every 8 hours) (see Simulated Profile in FIG. 1A to 1D) while maintaining the therapeutic plasma level of treprostinil.

FIG. 1E shows the measured and simulated PK profiles of free treprostnil solution (at 12 μg/kg) administered every 4 hours, QID. The plasma concentration reached a much higher peak (8.0 ng/mL) within one hour of treprostinil inhalation ($T_{max}$=0.083 hr) and dropped below the lower limit of quantification (LLOQ at 25 pg/mL) within 4 hours of treprostinil inhalation (FIG. 1E, Measured Data). This pK profile conforms with the dosing schedule listed in the prescribing information of inhaled Tyvaso (treprostinil), which is 4 times daily (QID) every 4 hours (FIG. 1E, Simulated Profile).

The BID or TID dosing schedule of liposomal treprostinil composition lead to a flatter plasma profile and a lower P/T ratio (less than 10) compared to that of the QID dosing schedule of free treprostinil solution (P/T ratio=121) (see Table 4).

TABLE 4

The peak-to-trough (P/T) ratio of liposomal treprostinil composition and free treprostinil solution inhaled by rats at different dosing schedule

| Formulation | Applied dose level | Schedule | $C_{max}$ (ng/mL) | $C_{last}$ (ng/mL) | P/T ratio[1] |
|---|---|---|---|---|---|
| Liposomal Treprostinil Composition | 48 μg/kg | 8 hrs, BID | 4.936 (at 8.33 h) | 2.134 (at 16 h) | 2.3 |
| | | 10 hrs, BID | 4.008 (at 10.33 h) | 1.075 (at 20 h) | 3.7 |
| | | 12 hrs, BID | 3.391 (at 12.33 h) | 0.363 (at 24 h) | 9.3 |
| | | 8 hrs, TID | 4.936 (at 8.33 h) | 2.134 (at 24 h) | 2.3 |
| Free Treprostinil Solution | 12 μg/kg | 4 hrs, QID | 7.971 (at 8.08 h) | Below LLOQ[2] (at 16 h) | NA |

1: P/T ratio = $C_{max}/C_{last}$, where $C_{max}$ = highest steady state plasma concentration and $C_{last}$ = lowest steady state plasma concentration between at least two doses.

2: Lower than the limit of quantification (LLOQ = 0.025 ng/mL)

3: Not available because of the undetectable $C_{last}$ 4 hours post dosing.

Example 2: The Effect of Liposomal Iloprost Composition on Iloprost Plasma Level in Healthy Rats After intra-tracheal administration of the liposomal iloprost composition (at 60 μg/kg), iloprost plasma concentration reached the peak $C_{max}$ (8.10 ng/mL) within 5 mins of dosing and decreased gradually to 0.32 ng/mL 8 hours post-dosing and 0.17 ng/mL 12 hours post-dosing (FIG. 2A to 2D, Measured Data). Therefore, the liposomal iloprost composition can be delivered twice a day (BID, every 6-8 hours) or three times a day (TID, every 6-8 hours) (see Simulated Profile in FIG. 2A to 2D) while maintaining therapeutic plasma level of iloprost.

Figure 2A:
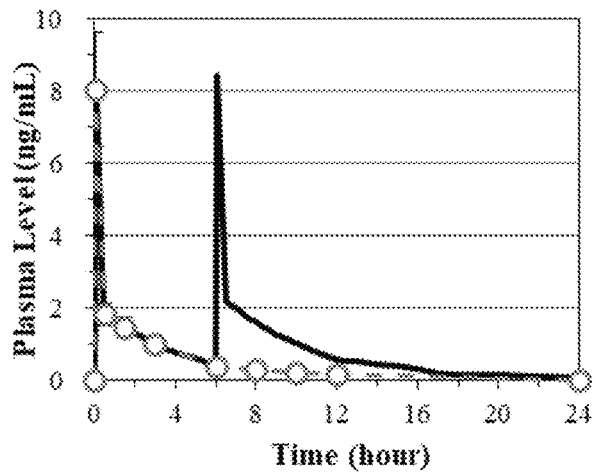
FIG. 2A-FIG. 2D are line graphs illustrating the simulated and measured iloprost plasma levels of the liposomal iloprost composition in rats at different dosing frequencies (FIG. 2A is 6 hours BID, FIG. 2B is 8 hours BID, FIG. 2C is the 6 hours TID and FIG. 2D is the 8 hours TID).
Figure 2B:
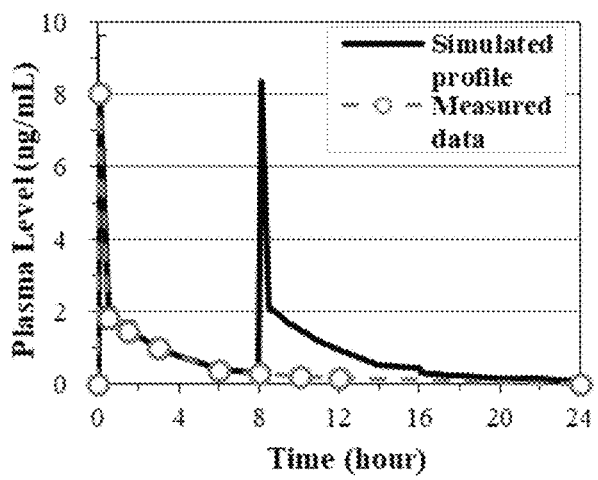
Figure 2C:
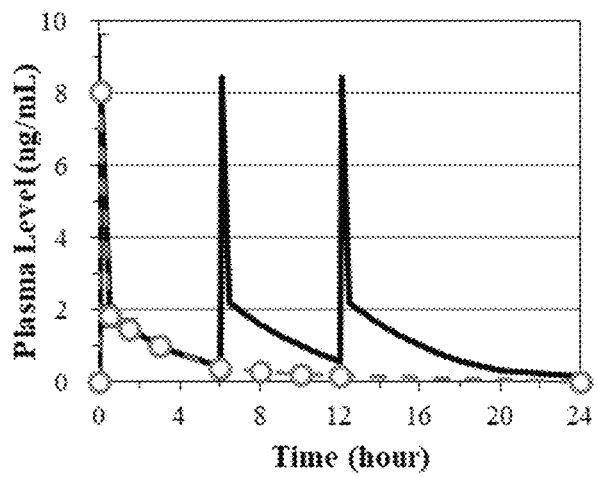
Figure 2D:
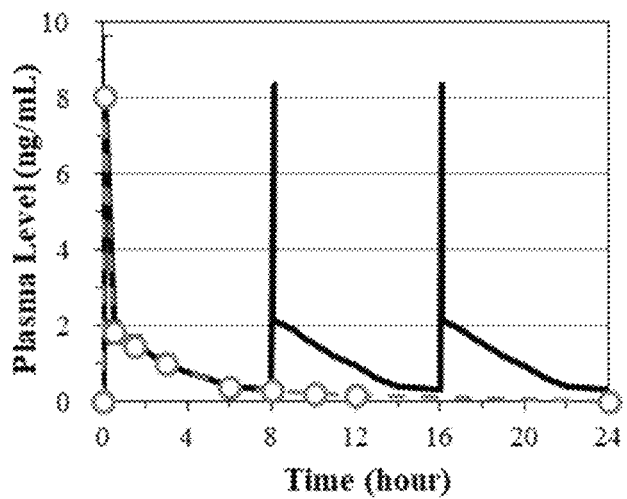
Figure 2E:
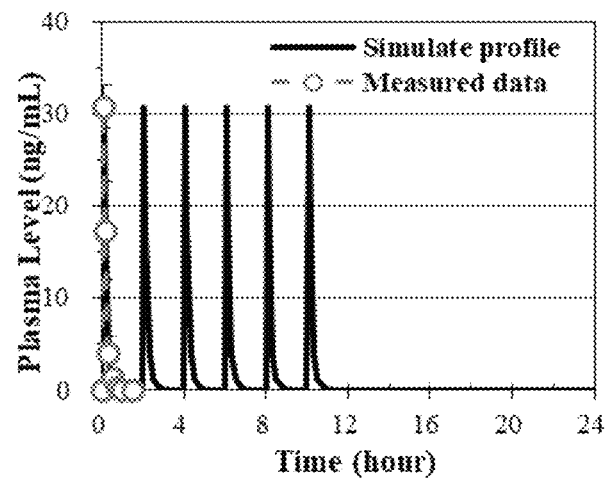
FIG. 2E is the line graph illustrating the simulated and measured iloprost plasma levels of the free iloprost solution in rats administered every 2 hours, 6 times a day.

The rat PK profile of free iloprsost solution (60 m/kg dose) shows a higher peak plasma concentration (32 ng/mL) was reached at 0.083 hr ($T_{max}$), similar to that of the liposomal iloprost composition but $C_{max}$ was approximately 4-fold of that of the liposomal iloprost composition. Iloprost plasma concentration dropped below LLOQ (100 pg/mL) within 1 hour post dosing (FIG. 2E, Measured Data). This pK profile conforms with the dosing schedule listed in the prescribing information of inhaled Ventavis (iloprost), which is 6-9 times daily (QID) every 2 hours (FIG. 2E, Simulated Profile).

The BID or TID dosing schedule of liposomal iloprost composition lead to a flatter plasma profile compared to that of the free iloprost solution administered 2 hourly (see Table 5).

TABLE 5

The peak-to-trough (P/T) ratio of liposomal iloprost composition and free iloprost solution administered to rats at different dosing schedules

| Formulation | Applied dose level | Schedule | $C_{max}$ (ng/mL) | $C_{last}$ (ng/mL) | P/T ratio[1] |
|---|---|---|---|---|---|
| Liposomal Iloprost Composition | 60 μg/kg | 6 hrs, BID | 8.431 (at 6.08 h) | 0.563 (at 12 h) | 15.0 |
| | | 8 hrs, BID | 8.352 (at 8.08 h) | 0.428 (at 16 h) | 19.5 |
| | | 6 hrs, TID | 8.431 (at 6.08 h) | 0.563 (at 18 h) | 15.0 |
| | | 8 hrs, TID | 8.352 (at 8.08 h) | 0.316 (at 24 h) | 26.4 |
| Iloprost Solution | 60 μg/kg | 2 hrs, 6 times per day | 30.750 (at 8.08 h) | Below LLOQ[2] (at 12 h) | NA[3] |

1: P/T ratio = $C_{max}/C_{last}$, where $C_{max}$ = highest steady state plasma concentration and $C_{last}$ = lowest steady state plasma concentration between at least two doses.
2: Lower than the limit of quantification (LLOQ = 0.1 ng/mL)
3: Not available because of the undetectable $C_{last}$ 2 hours post dosing.

Example 3: The Effect of Liposomal Treprostinil Composition on Treprostinil Plasma Level in Healthy Human The human PK profile of the inhaled liposomal treprostinil composition (102 μg emitted dose) shows the plasma treprostinil concentration was maintained between 0.12 to 0.26 ng/mL 8 hours post dosing, and gradually decreased to 0.02 ng/mL 12 hours post-dosing (FIG. 3A to 3D, Measured Data). Therefore, the liposomal composition of the present invention can be administered twice daily (BID, every 8, 10 and 12 hour) or three times daily (TID, every 8 hours) (FIG. 3A to 3D, Simulated Profile) while maintaining therapeutic plasma level of treprostinil.

The BID or TID dosing schedule of liposomal treprostinil composition in human lead to a flatter plasma profile and a lower P/T ratio (less than 15) compared to that of the QID dosing schedule of free treprostinil solution in human(P/T ratio=845) (see Table 6).

Figure 3A:
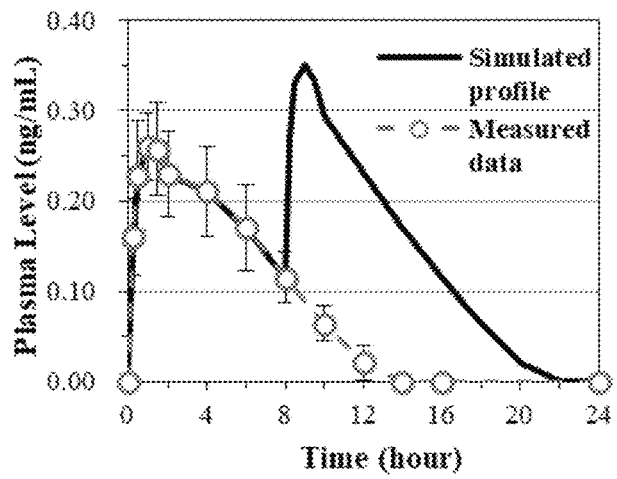
FIG. 3A-FIG. 3D are line graphs illustrating the simulated and measured treprostinil plasma levels of the liposomal treprostinil (Tyvaso) composition in human at different dosing frequencies (FIG. 3A is 8 hours BID, FIG. 3B is 10 hours BID, FIG. 3C is 12 hours BID and FIG. 3D is 8 hours TID).
Figure 3B:
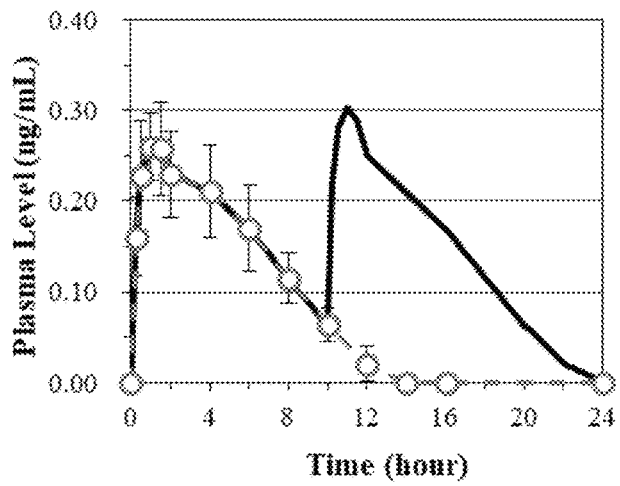
Figure 3C:
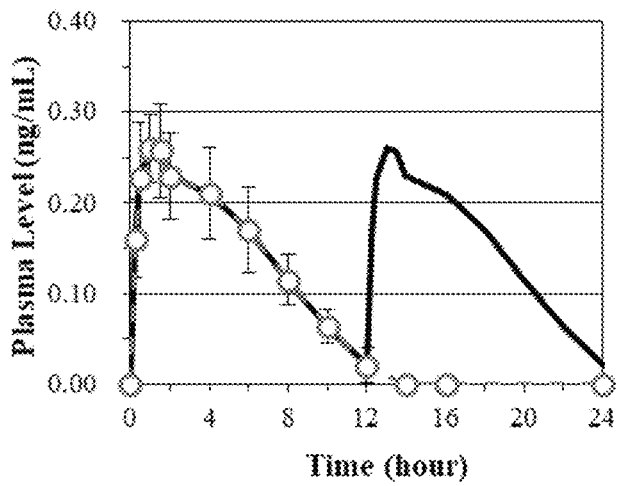
Figure 3D:
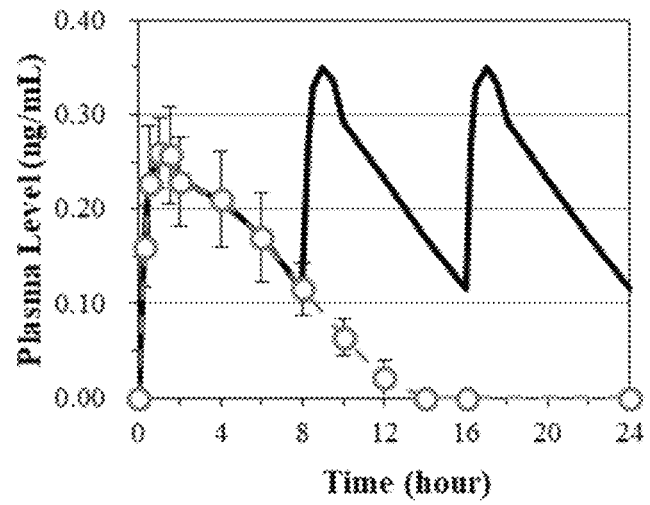
Figure 3E:
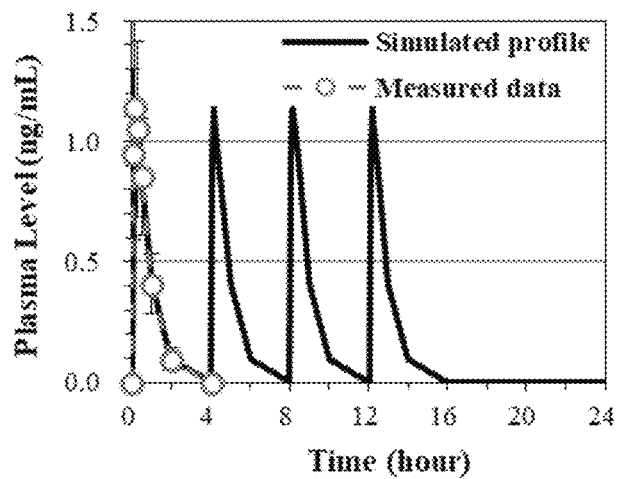
FIG. 3E is the line graph illustrating the simulated and measured treprostinil plasma levels of the free Tyvaso solution in human administered every 4 hours, QID.

The reference data of free Tyvaso (treprostinil) solution (54 μg/kg) in FIG. 3E was extracted from the published Phase I single dose escalation study in healthy volunteers [*Drug Design, Development and Therapy* 2012:6 19-28], which shows a higher peak plasma concentration (0.845 ng/mL) was reached at 0.167 hr ($T_{max}$) and dropped to 100 pg/mL 4 hours post administration. The simulated profile of free Tyvaso (treprostinil) solution in FIG. 3E was estimated based the reference data of free Tyvaso and conforms with the dosing schedule listed in the prescribing information of inhaled Tyvaso, which is 4 times daily (QID) scheduled every 4 hours.

TABLE 6

The peak-to-trough (P/T) ratio of liposomal treprostinil compositions in human at different dosing schedules

| Formulation | Applied dose level | Schedule | $C_{max}$ (ng/mL) | $C_{last}$ (ng/mL) | P/T ratio[1] |
|---|---|---|---|---|---|
| Liposomal Treprostinil Composition | 102 μg | 8 hrs, BID | 0.350 (at 9 h) | 0.115 (at 16 h) | 3.0 |
| | | 10 hrs, BID | 0.303 (at 11 h) | 0.064 (at 20 h) | 4.7 |
| | | 12 hrs, BID | 0.260 (at 12 h) | 0.021 (at 24 h) | 12.4 |
| | | 8 hrs, TID | 0.350 (at 9 h) | 0.115 (at 24 h) | 3.0 |
| Tyvaso (treprostinil) inhalation solution[2] | 54 μg | 4 hrs, QID | 0.845 (at 0.167 h) | 0.001 (at 16 h) | 845 |

1: P/T ratio = $C_{max}/C_{last}$, where $C_{max}$ = highest steady state plasma concentration and $C_{last}$ = lowest steady state plasma concentration between at least two doses.
2: Data obtained from Drug Design, Development and Therapy 2012:6 19-28

Example 4: The Effect of Liposomal Treprostinil Composition in PH Rats

The PK and PD profiles of the liposomal treprostinil composition is assessed in conscious rats with acute PH. A saline control group was included to confirm the reliability of the hypoxia-induced PH in rats. The PAP of the rats in the saline control group remained elevated for up to 12 hours.

PH Rats received free treprostinil solution at 6 μg/kg or the liposomal treprostinil composition at 6 μg/kg according to the methods described previously.

PH Rats received free treprostinil solution showed a mild reduction of PAP. The maximal effect (PAP reduced to 79% of baseline hypoxic value) was observed 0.5 hour post dosing and treprostinil plasma level was about 1 ng/mL.

Figure 4A:
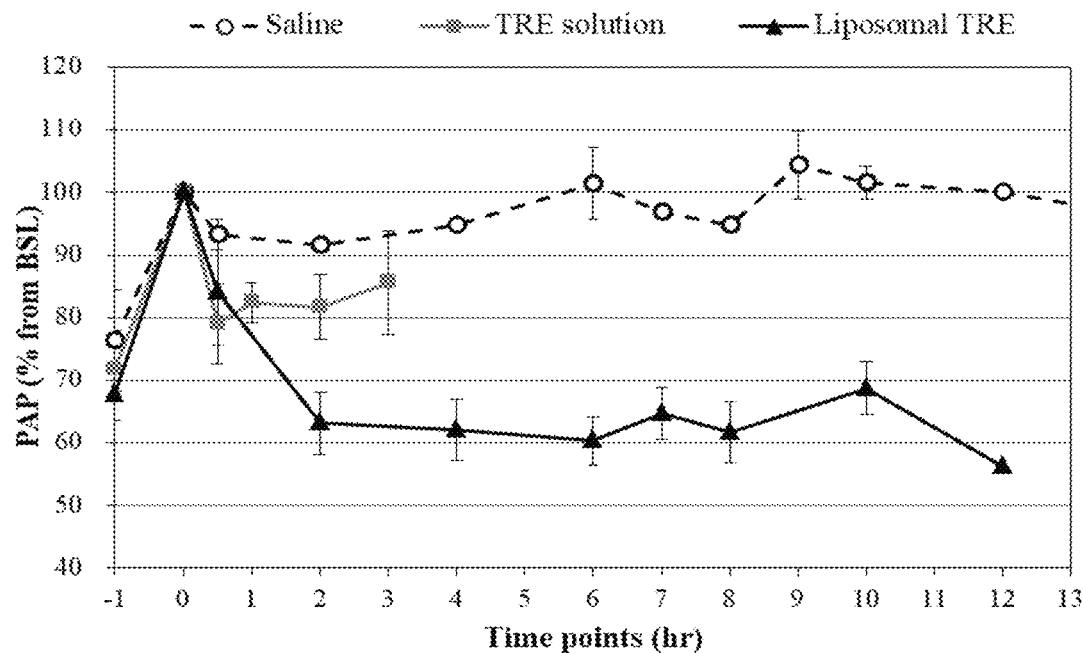
FIG. 4A is a line graph showing the reduction of PAP in PH rats administered with saline, free treprostinil solution (TRE Solution) or the liposomal treprostinil composition of the present invention (Liposomal TRE).

For PH rats treated with the liposomal treprostinil composition, the PAP was persistently lower than that of the rats treated with saline or free treprostinil solution. The lower PAP (PAP reduction to 69% of baseline hypoxic value) lasted up to 12 hours post-dosing (FIG. 4A). The results suggest that the liposomal trprostinil composition was more effectively to induce vasodilatation of the pulmonary artery in PH rats compare to the free treprostinil solution.

Figure 4B:
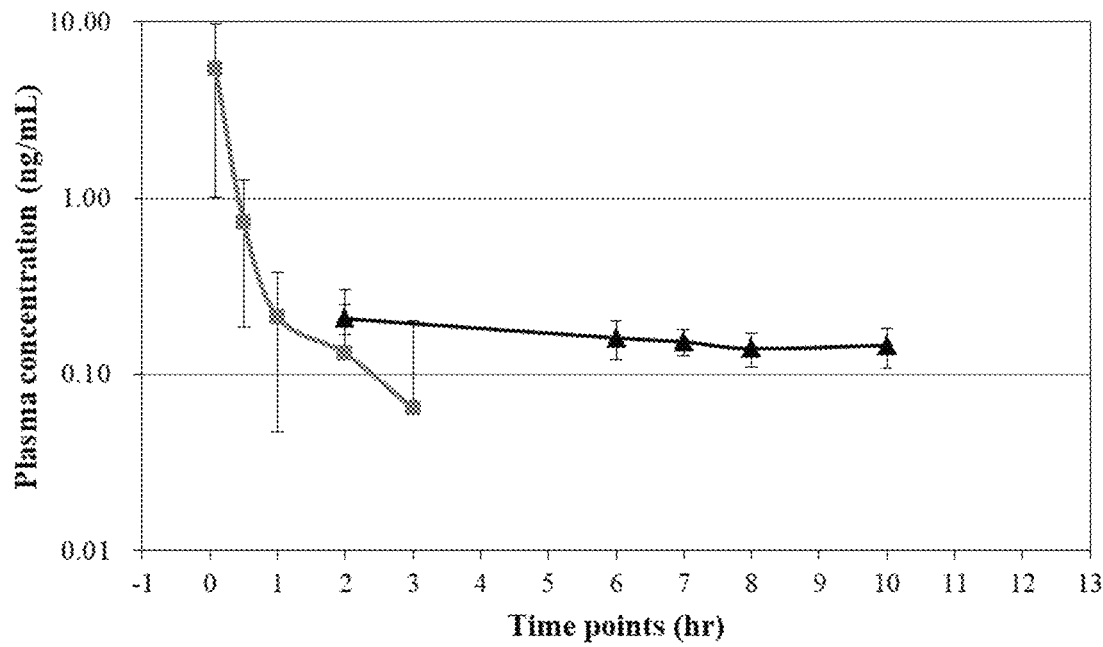
FIG. 4B is a line graph showing the treprostinil plasma concentration in PH rats administered with free treprostinil solution or the liposomal treprostinil composition.

In PH rats treated with liposomal treprostinil composition, the PK/PD profile data show treprostinil plasma concentration at about 0.1 ng/mL reduced PAP to 63% of the baseline hypoxic value. However, the same treprostinil plasma concentration (0.1 ng/mL) in rats treated with free treprostinil solution only reduced PAP to 83% of the baseline hypoxic value, see FIGS. 4A and 4B. For the same treprostinil plasma concentration, the free treprostinil solution is not as efficacious as the liposomal treprostinil composition in reducing PAP. Based on the PAP reduction potency definition set forth above, the liposomal treprostinil composition shows a 3-9-folds higher PAP reduction potency compared to that of the free treprostinil solution Table 7).

TABLE 7

PAP reduction potency of liposomal treprostinil composition and free treprostinil solution

| Sample | Applied dose level | Duration | AUC of PAP reduction (h*%)[1] | AUC of plasma conc. (h*ng/mL) | Potency[2] |
|---|---|---|---|---|---|
| Liposomal treprostinil Composition | 6 μg/kg | 3 hr | 80.89 | 1.17 | 69.1 |
| | | 8 hr | 270.17 | 1.25 | 216.1 |
| | | 10 hr | 339.69 | 1.53 | 222.0 |
| | | 12 hr | 414.73 | 1.77 | 234.3 |

TABLE 7-continued

PAP reduction potency of liposomal treprostinil composition and free treprostinil solution

| Sample | Applied dose level | Duration | AUC of PAP reduction (h*%)[1] | AUC of plasma conc. (h*ng/mL) | Potency[2] |
|---|---|---|---|---|---|
| Free Treprostinil solution | 6 μg/kg | 3 hr | 49.15 | 2.01 | 24.5 |

1. AUC of PAP reduction = the area under the curve of PAP reduction vs. time.
2. Potency = AUC of PAP reduction ÷ AUC of plasma conc..

Example 5: The Effect of Liposomal Iloprost Composition in PH Rats

PH Rats received free iloprost solution (2.5 μg/kg) showed a mild reduction of PAP. The maximal effect (PAP reduced to 76% of the baseline hypoxic value) was seen 0.75 hour post dosing and iloprost plasma level was below 0.1 ng/mL (LLOQ), see FIG. 5A.

Figure 5A:
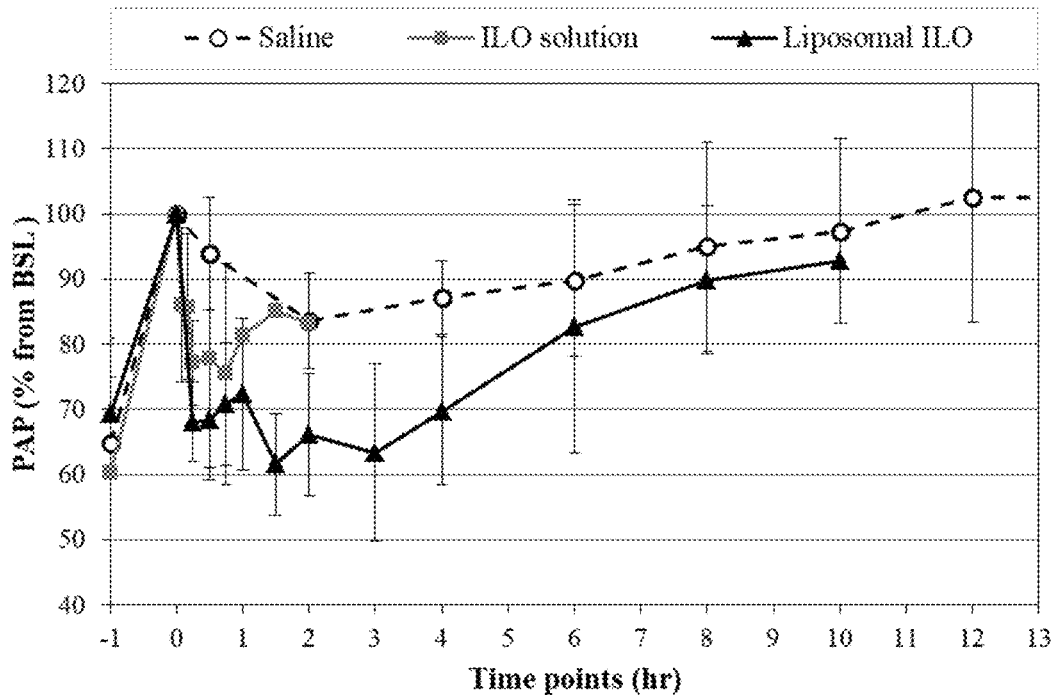
FIG. 5A is a line graph showing the reduction of PAP in PH rats administered with saline, free iloprost solution (ILO Solution) or the liposomal iloprost composition of the present invention (Liposomal ILO).

PH rats treated with the liposomal iloprost composition (2.5 μg/kg) had a persistently lower PAP than that of the rats treated with saline or free treprostinil solution. The lower PAP (PAP reduction to 70% of the baseline hypoxic value) lasted up to 4 hours post-dosing (FIG. 5A). The results suggest that the liposomal iloprost composition effectively induced vasodilatation of the pulmonary artery in PH rats.

Figure 5B:
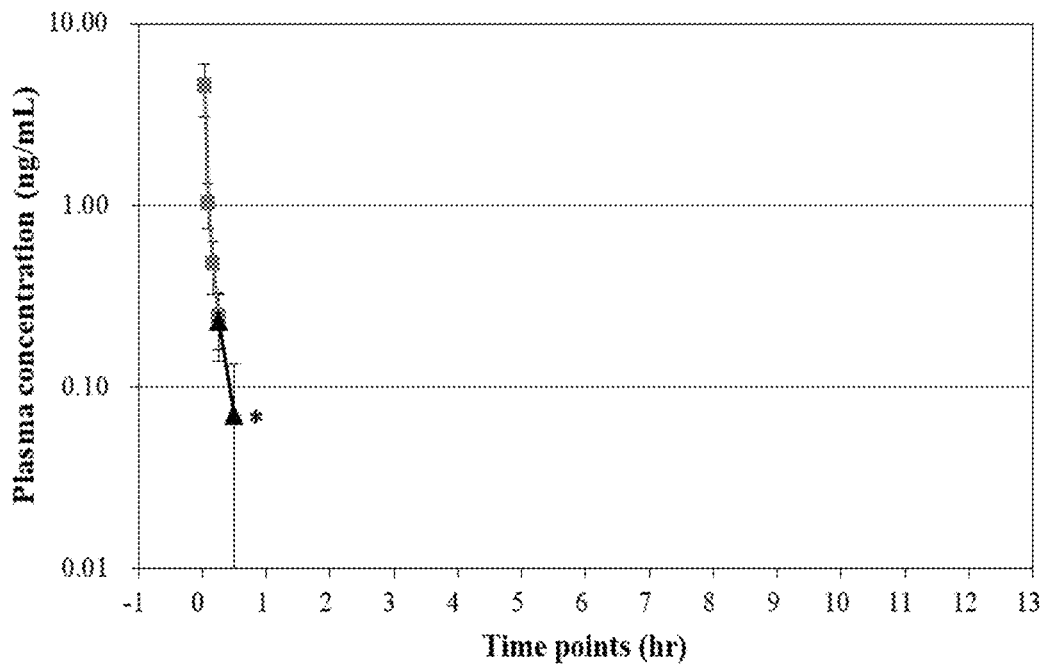
FIG. 5B is a line graph showing the iloprost plasma concentration in PH rats administered with free iloprost solution or the liposomal iloprost composition. (* The mean plasma concertation from 5 studied rats which 2 of them had drug level below the lower limit of quantification (LLOQ) at 0.25 hr and regarded as 0.)

The PK/PD profile data show that in PH rats treated with the liposomal iloprost composition, plasma concentrations near 0.1 ng/mL reduced the PAP to 68.4% of the baseline hypoxic value whereas similar iloprost plasma concentration (below LLOQ) of in rats treated with free iloprost solution does not seem to be as efficacious (reduced the PAP to 77.2% of the baseline hypoxic value) as the liposomal counterpart, see FIGS. 5A and 5B. Based on the PAP reduction potency definition set forth above, the liposomal iloprost composition shows a 3-5 folds higher PAP reduction potency compared to that of the free iloprost solution (see Table 8).

TABLE 8

PAP reduction potency of liposoma iloprost and free iloprost solution

| Sample | Applied dose level | Duration | AUC of PAP reduction (h*%)[1] | AUC of plasma conc. (h*ng/mL) | Potency[2] |
|---|---|---|---|---|---|
| Liposomal iloprost Composition | 2.5 µg/kg | 2 hr | 61.20 | 0.08[3] | 765.0 |
|  |  | 6 hr | 177.35 | 0.36[3] | 492.6 |
|  |  | 8 hr | 204.75 | 0.39[3] | 525.0 |
| Iloprost solution | 2.5 µg/kg | 2 hr | 36.44 | 0.24 | 151.8 |

1. AUC of PAP reduction = the area under the curve of PAP reduction vs.time.
2. Potency = AUC of PAP reduction ÷ AUC of plasma conc..
3. Because of the limitation of iloprost detection in plasma, the AUC of plasma concentration vs. time is calculated from a separate study with higher dose level (60 µg/kg). Accumulated AUC at 2.5 µg/kg dose level = Accumulated AUC at 60 µg/kg dose level × (2.5/60)

The invention claimed is:

1. A pharmaceutical composition, comprising:
   liposomes suspended in an external medium, said liposomes formed from (a) an external lipid bilayer and (b) an internal aqueous medium,
   wherein the external lipid bilayer is formed of a mixture of hydrogenated soy phosphatidylcholine (HSPC), one of distearyloyl phosphatidylglycerol (DSPG) or PEG-DSPE, and, cholesterol
   wherein the internal aqueous medium comprising a weak acid drug selected from treprostinil or iloprost and a bicarbonate salt in a concentration of about 50 mM to about 600 mM to provide a pH of the internal aqueous medium about 7 to 10 and a pH of the external medium that is greater than the pKa of treprostinil or the pKa of iloprost, respectively, and less than 6,
   wherein the external lipid bilayer has about 75-99 mole % of the HSPC: about 0-14.9 mole % of cholesterol: about 0.1-25 mole % of DSPG or PEG-DSPE, and
   wherein the pharmaceutical composition is characterized by exhibiting a P/T ratio of about 1 to about 100 at least six hours after administering to a subject, where P is a highest steady state plasma concentration of the weak acid drug and T is a lowest steady state plasma concentration of the weak acid drug, and said P/T ratio indicates that the pharmaceutical composition enhances the potency of the weak acid drug compared to a free weak acid drug and sustains the therapeutic effect of the weak acid drug for at least 6 hours.

2. The pharmaceutical composition of claim 1, wherein said weak acid drug is iloprost and the P/T ratio is about 5 to about 40.

3. The pharmaceutical composition of claim 1, wherein said weak acid drug is treprostinil and the P/T ratio is about 1 to about 20.

4. The pharmaceutical composition of claim 1, wherein the potency of the weak acid drug in the pharmaceutical composition is at least two times more than that of a free weak acid drug.

5. A method of treating pulmonary hypertension, comprising the steps of administering the pharmaceutical composition of claim 1 to a subject in need thereof at least every 6 hours, wherein the potency of said weak acid drug is enhanced compared to that of the free weak acid drug, wherein the pharmaceutical composition is administered orally, by inhalation or by injection.

6. The method of claim 5, wherein the pharmaceutical composition is administered once, twice or three times a day.

7. The method of claim 5, wherein the pharmaceutical composition is administered by inhalation.

8. The method of claim 7, wherein the peak to trough drug plasma concentration ratio (P/T ratio) is about 1 to about 40 from about 1 hour to about 12 hours after administration of the pharmaceutical composition to the subject.

9. The method of claim 5, further comprising administering at least one other agent effective to treat pulmonary hypertension.

10. The pharmaceutical composition of claim 1, wherein the external lipid bilayer is formed of a mixture of HSPC, PEG-DSPE, and cholesterol.

11. The pharmaceutical composition of claim 1, wherein the external lipid bilayer is formed of a mixture of HSPC, DSPG, and cholesterol.

12. A liposomes suspended in an external medium, said liposomes formed from (a) an external lipid bilayer and (b) an internal aqueous medium,
   wherein the external lipid bilayer is formed of a mixture of hydrogenated soy phosphatidylcholine (HSPC), one of distearyloyl phosphatidylglycerol (DSPG) or PEG-DSPE, and, cholesterol
   wherein the internal aqueous medium comprising a weak acid drug selected from treprostinil or iloprost and a bicarbonate salt in a concentration of about 50 mM to about 600 mM to provide a pH of the internal aqueous medium about 7 to 10 and a pH of the external medium that is greater than the pKa of treprostinil or the pKa of iloprost, respectively, and less than 6,
   wherein the molar ratio HSPC:cholesterol:DSPG or PEG-DSPE is 3:2:0.075,
   wherein the pharmaceutical composition is characterized by exhibiting a P/T ratio of about 1 to about 100 at least six hours after administering to a subject, where P is a highest steady state plasma concentration of the weak acid drug and T is a lowest steady state plasma concentration of the weak acid drug, and said P/T ratio indicates that the pharmaceutical composition enhances the potency of the weak acid drug compared to a free weak acid drug and sustains the therapeutic effect of the weak acid drug for at least 6 hours.

13. A pharmaceutical composition comprising:
   liposomes suspended in an external medium, said liposomes formed from (a) an external lipid bilayer and (b) an internal aqueous medium,
   wherein the external lipid bilayer is formed of a mixture of a hydrogenated soy phosphatidylcholine (HSPC) and PEG-DSPE, wherein the internal aqueous medium comprising iloprost and a bicarbonate salt in a concentration of about 50 mM to about 600 mM to provide a pH of the internal aqueous medium about 7 to 10 and a pH of the external medium that is greater than the pKa of iloprost, and less than 6,
   wherein the external lipid bilayer has about 75-99 mole % of the HSPC: about 0.1-25 mole % of PEG-DSPE, and
   wherein the pharmaceutical composition is characterized by exhibiting a P/T ratio of about 1 to about 100 at least six hours after administering to a subject, where P is a highest steady state plasma concentration of iloprost and T is a lowest steady state plasma concentration of iloprost, and said P/T ratio indicates that the pharmaceutical composition enhances the potency of the iloprost compared to free iloprost and sustain the therapeutic effect of the iloprost at least 6 hours.

14. The pharmaceutical composition of claim 13, wherein the pH of the internal aqueous medium is about 8 to 9.

15. The pharmaceutical composition of claim 13, wherein the external lipid bilayer has about 98 mole % of the HSPC: about 2 mole % of the PEG-DSPE.

16. The pharmaceutical composition of claim 1, wherein the pH of the internal aqueous medium is about 8 to 9.

17. A method of treating pulmonary hypertension, comprising the steps of administering the pharmaceutical composition of claim 12 to a subject in need thereof at least every 6 hours, wherein the potency of said weak acid drug is enhanced compared to that of the free weak acid drug, wherein the pharmaceutical composition is administered orally, by inhalation or by injection.

18. The method of claim 17, wherein the pharmaceutical composition is administered once, twice or three times a day.

19. The method of claim 17, wherein the pharmaceutical composition is administered by inhalation.

20. The method of claim 19, wherein the peak to trough drug plasma concentration ratio (P/T ratio) is about 1 to about 40 from about 1 hour to about 12 hours after administration of the pharmaceutical composition to the subject.

21. The method of claim 17, further comprising administering at least one other agent effective to treat pulmonary hypertension.

22. A method of treating pulmonary hypertension, comprising the steps of administering the pharmaceutical composition of claim 13 to a subject in need thereof at least every 6 hours, wherein the potency of said weak acid drug is enhanced compared to that of the free weak acid drug, wherein the pharmaceutical composition is administered orally, by inhalation or by injection.

23. The method of claim 22, wherein the pharmaceutical composition is administered once, twice or three times a day.

24. The method of claim 22, wherein the pharmaceutical composition is administered by inhalation.

25. The method of claim 24, wherein the peak to trough drug plasma concentration ratio (P/T ratio) is about 1 to about 40 from about 1 hour to about 12 hours after administration of the pharmaceutical composition to the subject.

26. The method of claim 22, further comprising administering at least one other agent effective to treat pulmonary hypertension.

* * * * *